United States Patent [19]
Dulebohn

[11] Patent Number: 5,171,314
[45] Date of Patent: Dec. 15, 1992

[54] SURGICAL SNARE

[75] Inventor: David H. Dulebohn, Tonka Bay, Minn.

[73] Assignee: Andrew Surgical, Inc., Plymouth, Minn.

[21] Appl. No.: 557,591

[22] Filed: Jul. 24, 1990

[51] Int. Cl.⁵ ............................................. A61B 17/32
[52] U.S. Cl. ................................. 606/113; 606/110
[58] Field of Search ............... 606/110, 113, 169, 171; 128/749, 751

[56] References Cited

U.S. PATENT DOCUMENTS

| | | | |
|---|---|---|---|
| 1,833,687 | 11/1931 | Neivert | 606/113 |
| 2,054,149 | 9/1936 | Wappler | 606/113 |
| 2,856,933 | 10/1958 | Hildebrand et al. | 606/113 |
| 3,791,387 | 2/1974 | Itoh | 606/113 |
| 3,828,790 | 8/1974 | Curtiss et al. | 128/320 |
| 3,955,578 | 5/1976 | Chamness et al. | 128/303.15 |
| 4,256,113 | 3/1981 | Chamness | 128/303.14 |
| 4,294,254 | 10/1981 | Chamness | 128/303.14 |
| 4,326,530 | 4/1982 | Fleury, Jr. | 128/303.14 |
| 4,345,599 | 8/1982 | McCarrell | 128/320 |
| 4,493,320 | 1/1985 | Treat | 128/303.15 |
| 4,538,611 | 9/1985 | Kelman | 606/113 |
| 4,718,419 | 1/1988 | Okada | 128/303.15 |
| 4,732,150 | 3/1988 | Keener, Jr. | 128/320 |

Primary Examiner—Stephen C. Pellegrino
Assistant Examiner—Michael Rafa
Attorney, Agent, or Firm—Zarley, McKee, Thomte, Voorhees, & Sease

[57] ABSTRACT

An improved surgical snare apparatus includes an elongated tubular tip extending from a control handle. The ends of a single U-formed snare wire extend through the tip and out of its proximal end where they are secured to a control element in the handle that enables moving of the wire. The distal end is modified from conventional snares to allow the contracted snare loop to be substantially nested within the tip. In the fully contracted nested position, the wire substantially closes the modified distal end so that the sharp cutting edges of the distal end are not exposed to contact with body tissue during insertion into an incision or opening. Thus, the combination of the modified distal end and the single wire nested within presented a tip the minimizes trauma during insertion.

The configuration of the expanded single wire loop is modified from conventional dual wire snare loops into a more rounded form which is easier to manipulate around tissue to be severed, a polyp for example.

19 Claims, 5 Drawing Sheets

_fig. 8_

_fig. 9_

_fig. 10_

_fig. 11_

SURGICAL SNARE

BACKGROUND OF THE INVENTION

A. Field of the Invention

The present invention relates to medical surgical instruments, and in particular, to surgical snare instruments.

B. Problems in the Art

Surgical snares have a wide variety of present uses. Examples are prostrate surgery, removal of tonsils, polyps and other operations where tissue must either be severed and/or removed.

Some examples of surgical snares can be found in the following U.S. patents:

| U.S. Pat. No. | Inventor | Issue Date |
| --- | --- | --- |
| 3,828,790 | Curtiss, et al. | August 13, 1974 |
| 3,955,578 | Chamness, et al. | May 11, 1976 |
| 4,256,113 | Chamness | March 17, 1981 |
| 4,294,254 | Chamness | October 13, 1981 |
| 4,326,530 | Fleury, Jr. | April 27, 1982 |
| 4,345,599 | McCarrel | August 24, 1982 |
| 4,493,320 | Treat | January 15, 1985 |
| 4,718,419 | Okada | January 12, 1988 |
| 4,732,150 | Keener, Jr. | March 22, 1988 |

While the above patents reveal a variety of different structures for surgical snares, little or nothing is said about the size ratio of the tube to the wire. Single wire snares illustrated in U.S. Pat. No. 4,732,150 would require a high ratio, because an extremely fine wire would be required to allow contracting the loop inside the cannula without permanent deformation of the wire. An extremely fine wire might be functional in some procedures, however, generally, the fine wire would lack the rigidity necessary to manipulate around and sever or retrieve tissue.

Another concern involves the dual wire snares revealed in the above patents. Dual wires are welded together at one end with the wires parallel. This eliminates the problem of permanent deformation when the loop is pulled into the cannula. However, the shape of the extended loop is extremely limited to a narrow elongated form.

Another undesirable feature of the designs illustrated in the above patents is that the distal ends of the cannulae are cut off square to the axes of the cannulae. This produces a blunt end which is traumatic to insert into an incision or opening.

There is, therefore, a real and significant need for snares that overcome the above objectionable features. It is the primary objective of the present invention to provide a means and method for improved single wire snares which are practical to use in a variety of procedures by virtue of the single snare wire being considerably larger in proportion to the size of the cannula as compared to those illustrated above.

Another object of the present invention is to produce an improved shape to the configuration of the loop in the fully extended and intermediate positions.

Another object of the present invention is to provide a means for less traumatic insertion of the instrument into the incision or opening, and provide a means for both cutting and retrieving tissue.

A still further object of the present invention is to provide a means and method as above described which is simple in structure, durable, efficient, safe, and economical.

These and other objects, features, and advantages of the present invention will become more apparent with reference to the accompanying specification and claims.

SUMMARY OF THE INVENTION

The present invention relates to an improved surgical snare. As is conventional, a handle, graspable and maneuverable by the surgeon, generally has a control means manipulatable by the surgeon to adjust the size of the snare loop from an expanded to a contracted state or vica versa. A tip, which is a cannula, extends from the handle. The free ends of a single U-formed wire extend through the hollow interior from the distal end and exit through the proximal end of the cannula.

The ends of the snare wire are attached to the control element on the handle. Pulling the control element proximally will contract the snare loop; whereas pushing it distally will expand the loop.

The invention includes a configuration at the distal end of the tip to allow the snare wire to be substantially nested within the distal end when contracted to its smallest contracted size. As nested, the wire substantially closes the opening in the distal end thus covering the sharp cutting edges of the tip. This presents a smooth closed end at insertion through a small opening or incision. Thus, instead of utilizing simply an open end of a cylindrical tube at the distal end, the distal end has a receiving means which allows reception of a substantial part of the contracted loop into the distal end. The loop itself therefore provides a sort of rounded surface that is only slightly larger than the outside diameter of the tip. The extension of the loop slightly beyond the end of the cannula covers the sharp edges of the tip end.

The receiving means of the tip end can take different forms and embodiments which are described in more detail later.

DETAILED DESCRIPTION OF THE PREFERRED EMBODIMENT

With reference to the accompanying drawings, a detailed description of the preferred embodiments of the present invention will now be set forth. It is to be understood that these preferred embodiments are intended to illustrate some of the forms the invention can take, but are not intended nor do they necessarily limit the scope of the invention at large.

Reference numerals will be utilized to indicate parts and locations throughout the drawings. The same reference numerals will be used for the same parts or locations in all the drawings unless otherwise indicated.

As generally described previously, the invention utilizes basically conventional-type surgical snare components in terms of a handle and an elongated tip end or cannula which is insertable into an incision or opening in a patient. The invention does, however, achieve its objectives by utilizing unique structure including a modified distal end of the instrument tip. This distal end allows the snare loop to be effectively and efficiently moved between expanded positions and a contracted position where it is substantially enveloped by the distal tip end. This allows a smooth, smaller diameter tip end, which presents less trauma when being inserted, utilized or retracted. It also allows a larger wire diameter, as compared with the tube diameter of the tip end, for better cutting or retrieving, and better durability. It also allows single wire loops to be used, and facilitates the easy and reliable formation of expanded loops of effective and usable size and form.

Figures 1, 2, 3, 4:
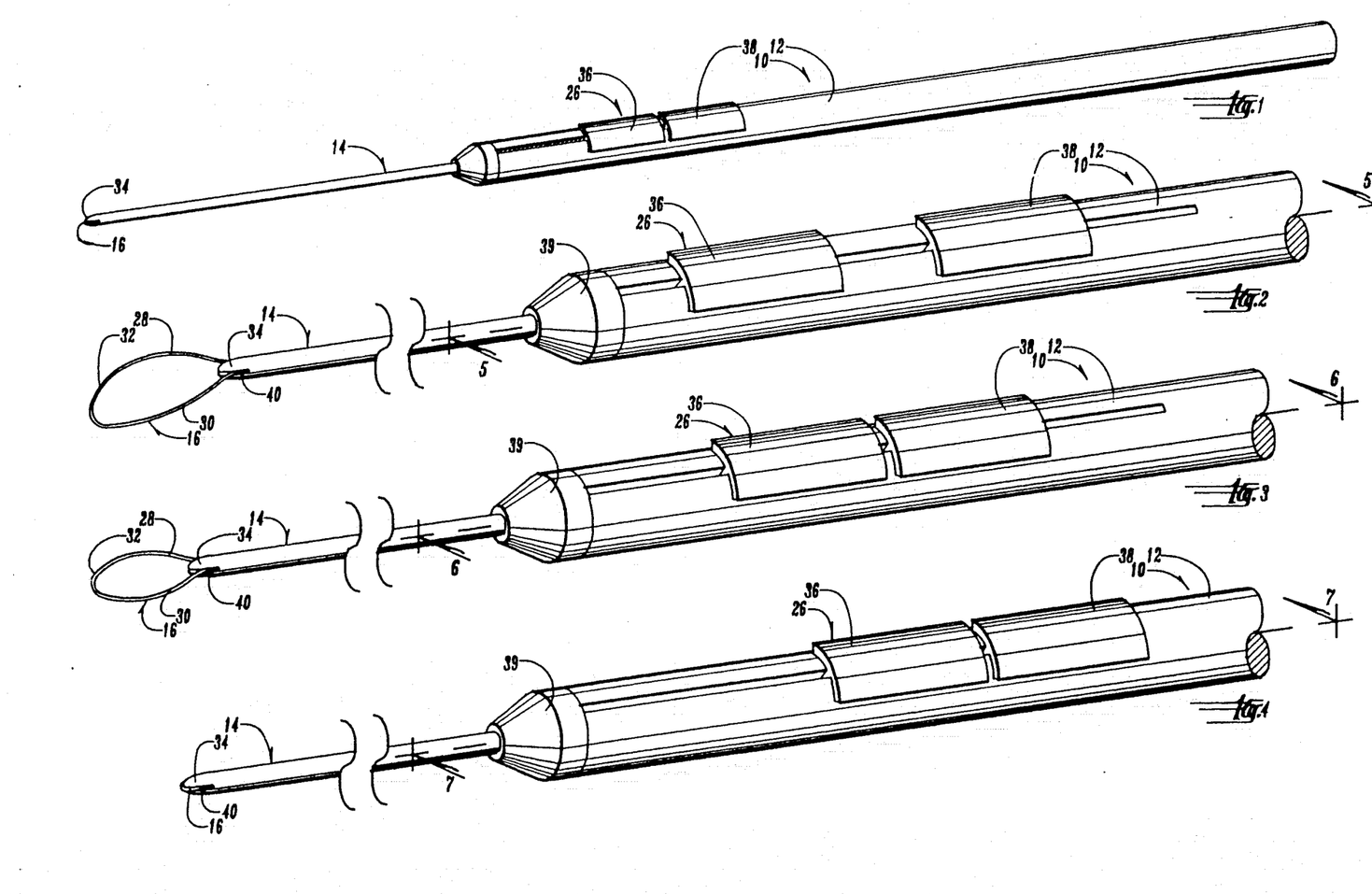
FIG. 1 is a perspective view of the surgical snare according to the present invention showing the surgical loop in a fully contracted state.
FIG. 2 is an enlarged partial perspective view of the snare of FIG. 1 but showing the loop in a fully expanded state.
FIG. 3 is a partial perspective view like FIG. 2 except showing the snare loop in an intermediate position.
FIG. 4 is a partial perspective view like FIGS. 2 and 3 except showing the surgical snare in a retracted or contracted position like shown in FIG. 1.
Figure 5:
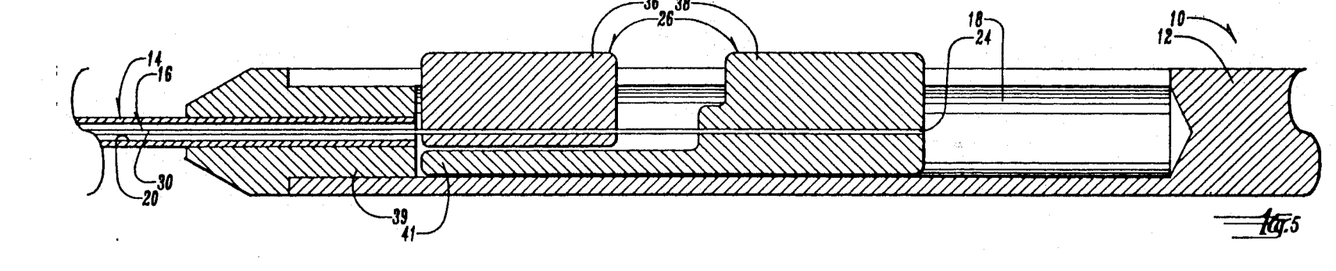
FIG. 5 is a cross sectional view taken along line 5—5 of FIG. 2.
Figure 6:
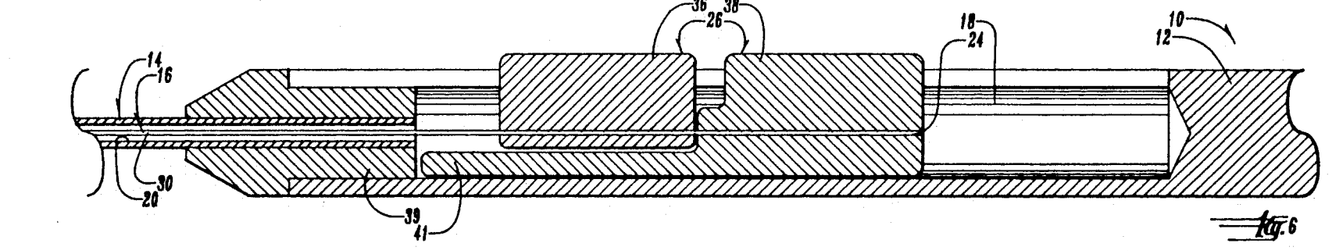
FIG. 6 is a cross sectional view taken along line 6—6 of FIG. 3.
Figure 7:
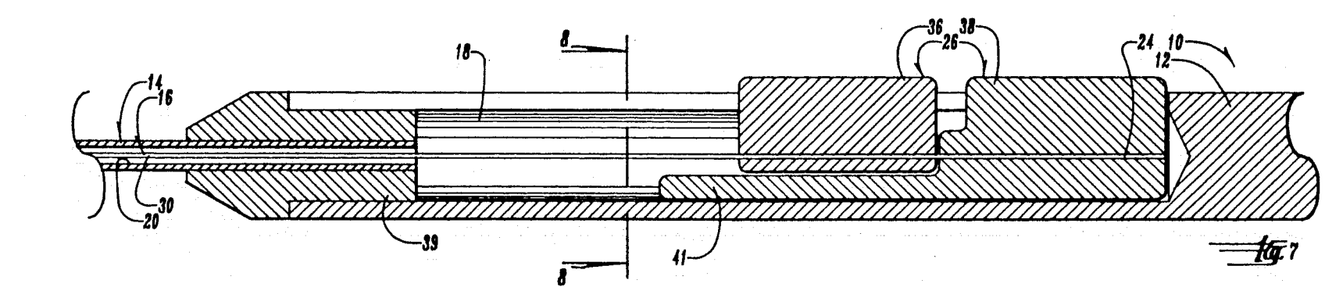
FIG. 7 is a cross sectional view taken along line 7—7 of FIG. 4.

A first preferred embodiment of the invention is shown in FIGS. 1-11. Referring particularly to FIG. 1, a surgical snare 10 is shown having a handle 12, a tip 14 with spherical formed distal end 34, and a snare wire 16. Both the handle and tip have hollow center bores 18 and 20 respectively (see FIGS. 5-8). Wire 16 has first and second free ends 22 and 24 which are connected to a control means 26 which is slidable along handle 12 (see FIGS. 5-9). Intermediate portions 28 and 30 of wire 16 extend through a portion of hollow bore 20 of handle 12 and through hollow bore 18 of tip 14. The loop end 32 of wire 16 is extendable out of distal end 34 through a slot 40 of tip 14 to perform cutting or retrieving surgical functions.

FIGS. 2-4 show in enlarged perspective pertinent portions of snare 10, and the general functional positions of snare 10. In FIG. 2, portions 36 and 38 of control means 26 are pushed to their forward-most positions on handle 12 to fully expand loop end 32. In this configuration, the snare instrument 10 and loop end 32 can be manipulated to surround tissue to be cut or retrieved.

By pulling portion 36 of control means 26 rearwardly or proximally on handle 12 to move it adjacent portion 38 of control means 26, such as shown in FIG. 3, the loop end 32 can be diminished in size to its somewhat intermediate position as shown in that drawing. This illustrates that some intermediate adjustment can be made in the size of loop end 32.

FIG. 4 shows the contracted state of loop end 32 accomplished by proximal movement of both portions 36 and 38 of control means 26 to their rearward most positions on handle 12. In this position, tissue can be cut by virtue of the snare wire 16 being pulled through the tip distal end 34 which would cause severing to occur of the tissue against distal end 34. Alternatively, loop end 32 can surround matter and by pulling loop 32 towards distal end 34 it can be secured and therefore retrieved by snare instrument 10.

In the embodiment shown in FIGS. 1-4, the two portions 36 and 38 of control means 26 are two separate control slides which are somewhat independently movable from one another. Free end 22 of wire 16 is connected to slide 36 (see FIG. 9) by means known in the art (for example adhesive or welding), whereas end 24 is connected to slide 38 (see FIG. 9). By moving slides 36 and 38 together to the positions of FIG. 4 the contracted loop end of wire 16 in FIG. 4 can be accomplished.

If it is desired to enlarge the loop of wire 16, control slide 38 can then be moved distally (which would also push control slide 36 with it) until portion 41 of slide 38 comes into abutment with ferrule 39. This achieves modification and enlargement of the loop (see FIGS. 3 and 6). Slide 36 can then be moved further towards tip 14 until it also abuts ferule 39 to produce further modification and expansion of the loop configuration (see FIGS. 2 and 5). These moves produce what can be called differential motion between slides 36 and 38 to produce a variety of configurations of loop end 32.

It is pointed out that the arrangement of snare 10 allows for one unitary piece of snare wire 16 to be used. This eliminates the need for some how connecting two wire portions However, the present invention is not limited to a one piece snare wire 16.

Figure 8:
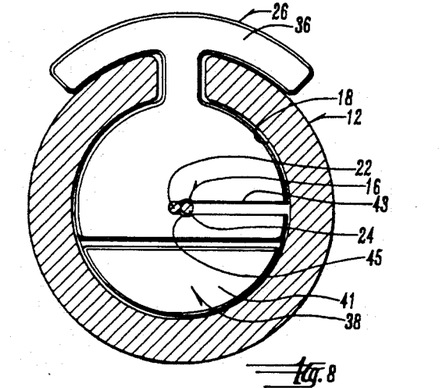
FIG. 8 is a cross sectional view taken along line 8—8 of FIG. 7.
Figure 9:
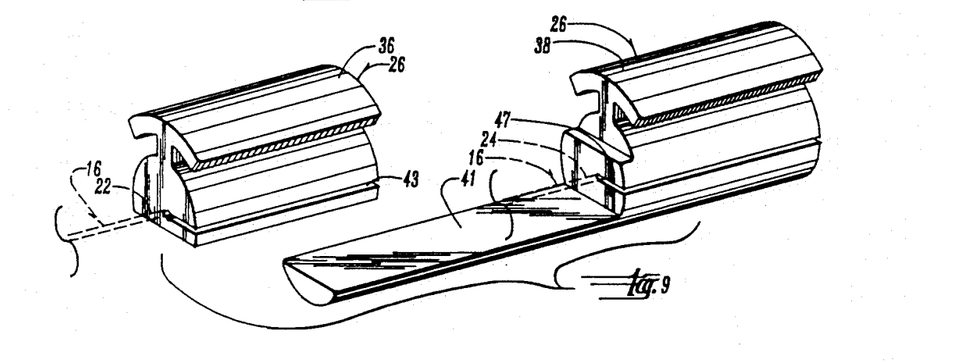
FIG. 9 is an exploded isolated perspective view of the control elements of the embodiment of the invention shown in FIGS. 1-8.

FIGS. 8 and 9 show how the two slides 36 and 38 are configured in the preferred embodiment, and how they are assembled into the handle 12. It is noted that free end 22 of wire 16 is inserted into slot 43 of slide 36 and secured thereto. Free end 24 of wire 16, however, can freely and slideably pass through slot 43 when assembled, by virtue of enlarged longitudinal channel 45 (large enough in diameter to let free end 24 freely pass). End 24 is then secured in slot 47 of slide 38.

Figure 10:
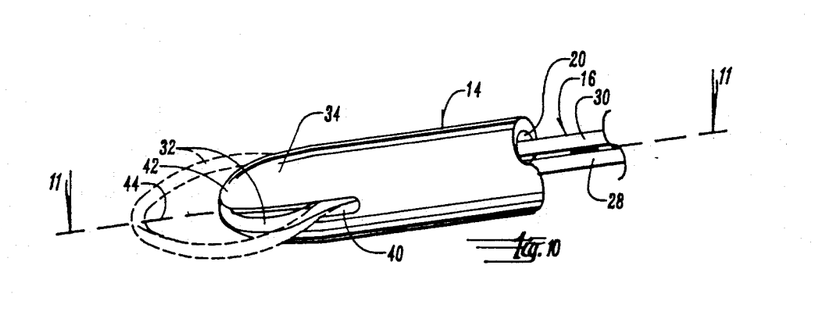
FIG. 10 is a partial perspective view of the tip end of the embodiment of FIGS. 1-8 showing in solid lines the loop in a contracted state, and in dashed lines the loop in a more expanded state.
Figure 11:
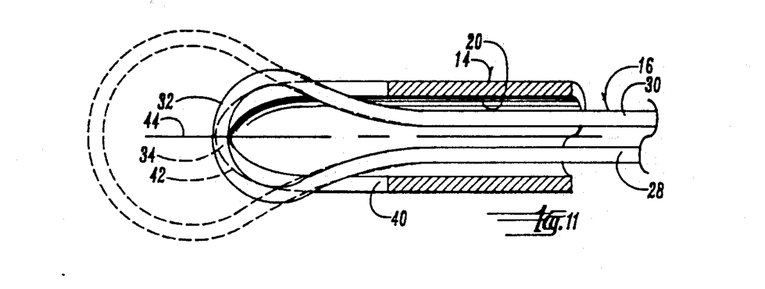
FIG. 11 is a sectional view taken along line 11—11 of FIG. 10.

FIGS. 10 and 11 show in more detail one of the important features of this preferred embodiment of the present invention. Distal end 34 is not simply an open blunt end of a cylindrical tube. As can be seen, it is a hemispherically formed tip including a slot 40 that extends proximally from the very end 42 of distal end 34 along the longitudinal axis 44 of tip 14. The slot is aligned so that each side of loop end 32 can matingly extend through opposite sides of the slot 40.

By referring to FIG. 10, loop end 32 is shown in solid lines in its most contracted state. It can be seen that slot 40 allows loop end 32 to be drawn in substantially into distal end 34 of tip 14. The outer rounded surfaces, however, of loop end 32 are still allowed to extend slightly beyond the outside diameter of distal end 34. Basically, as has been previously described, all conventionally known wire type materials used for surgical snares need properties such as some rigidness, strength, and durability, but they are generally made of metal or perhaps some types of plastics. However, in each case, they have a limit of elasticity. This means that these wires can not be bent to a shape where the loop end 32 is basically no more than wire 16 being side by side so that the loop part is basically eliminated. If this were done, the limit of elasticity on the wire material would be breached and it would result in permanent deformation. This means that the wire would not return back to a loop-type shape such as shown in FIGS. 2 and 3; but would be permanently creased and therefore would not function effectively.

Therefore, slot 40 allows loop end 32 to be contracted as far as possible without exceeding its limits of elasticity; while at the same time allowing it to be retracted into distal end 34 at least substantially and therefore achieves a much more unitary configuration with distal end 34 which provides for smoother entry through small openings or incisions in surgery. Consequently, this snare, unlike more conventional snares, plays as big a role in limiting trauma at insertion during surgery, and at withdrawl with respect to the incision or opening.

The invention also produces better loop configuration and allows greater flexibility in manipulating loop end 32 between its enlarged and contracted states. This is also accomplished with a minimum of structure and manufacturing cost and also does not increase the risk or potential for malfunction, breakage, and the like.

Moreover, the configuration does allow design of a smaller diameter tip 14 which furthermore allows the use of smaller incisions and openings for the instrument.

It is to be noted that the limitations as to the diameter of hollow bore 20 of tip 14 is basically that of the diameter of wire 16. It must be understood that for certain surgical snare procedures, the diameter of wire 16 cannot be less than a certain specification. Therefore, viewed in a different light, the present invention can allow as small as possible inside diameter for hollow bore 20 by the utilization of what would be called the receiving means or slot 40 as previously described. This is also a way to reduce the entire outside diameter of tip 14.

Wire 16, in the preferred embodiment, can be any conventional surgical snare wire. It can be a type of metal, (for example stainless steel), certain types of plastics, or even carbon fiber. Furthermore, certain types of metal materials can be welded together to form a composite wire.

Additionally, it is understood that special types of wires can be used. For example, special shape memory effect wire, for example Nitinol, available from Special Metals, Inc., Middle Settlement Road, New Hartford, N.Y. 13413, could be utilized in a fashion to form even smaller contracted loop ends 32; in turn allowing even smaller diameters for tip 14. This is described in co-owned and co-pending U.S. patent application Ser. No. 07/557,536, filed Jul. 24, 1990, and entitled "Surgical Snare With Shape Memory Effect Wire" which is incorporated by reference herein.

It is to be appreciated that the invention can be used in many surgical procedures, for example prostrate surgery, removal of tonsils, sinus and cancer operations, and the like. It can also be used in a retrieving sense for procedures such as orthoscopic surgery.

The invention does adopt itself to other configurations. Another preferred embodiment is shown in FIGS. 12-16. A surgical snare 46 has a handle (not shown), tip 50, and wire 52. In this case, the differential control member of FIG. 4 can again be used. Alternatively a single control member (not shown) to which both first and second ends of wire 52 are attached, and is slidable along handle 48 could be used. Such a single control is disclosed in the above mentioned application Ser. No. 07/557,536 filed Jul. 24, 1990.

The function of this embodiment is generally similar to that of FIGS. 1-11 except as follows. As can be seen in FIGS. 12-16, distal end 60 includes a closed hemispherical end cap 62, and a side opening 64 (through which loop end 66 of wire 52 extends). Still further, a slot 68 extends along longitudinal axis 70 proximally from side opening 64.

Figure 12:
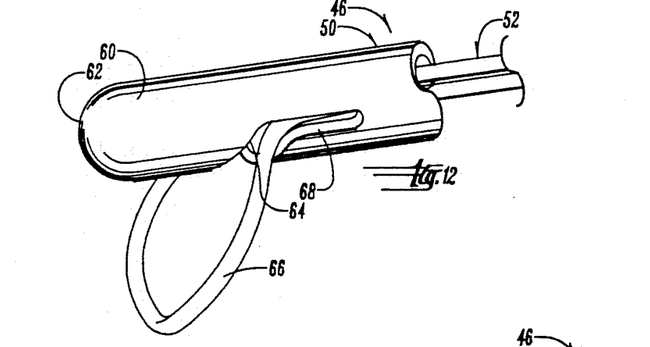
FIG. 12 is an enlarged partial perspective view of an alternative embodiment for a tip end with the surgical loop shown in an angled fully expanded state.
Figure 13:
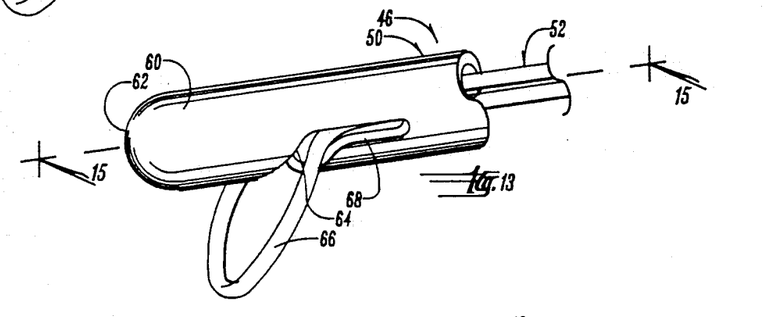
FIG. 13 is similar to FIG. 12 except showing the loop end in an intermediately expanded, angled state.
Figure 14:
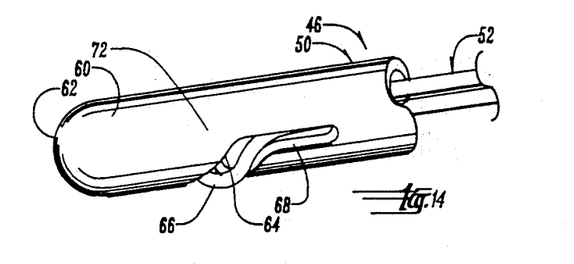
FIG. 14 is similar to FIGS. 12 and 13 except showing the loop end in a retracted state.
Figure 15:
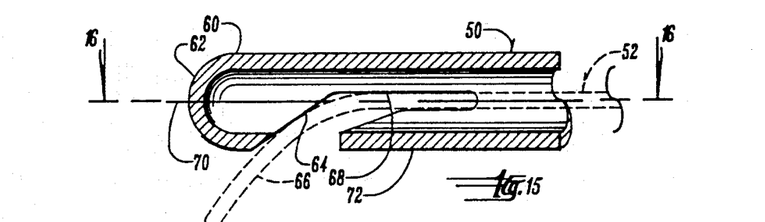
FIG. 15 is a cross sectional view taken along lines 15—15 of FIG. 13.
Figure 16:
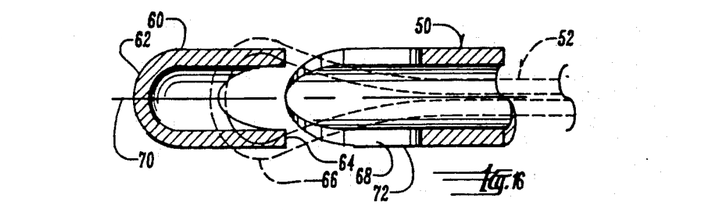
FIG. 16 is a cross sectional view taken along lines 16—16 of FIG. 15.

Also, it is noted that side opening 64 is actually angled from outer surface 72 of tip 50 inwardly and proximally to axis 70.

The embodiment of FIGS. 1-11 is basically a cutting snare. Loop end 32 surrounds a mass of tissue. Slides 36 and 38 of control means 26 are slid proximally to pull the mass against distal end 34 which performs a cutting or severing action. Snare 46 of FIGS. 12 through 16 is a retrieving snare. It does not have the direct countervailing force of the wire 52 being pulled directly against tip end. Rather, the loop end 66 slides angularly out of side opening 64 and can achieve an enlarged loop which can surround the piece of tissue or other matter. Movement of the control member(s) (not shown) proximally will then cinch loop end 66 around the item and pull it against the side of distal end 60. The entire instrument can then be withdrawn.

The "receiving means" of embodiment 46 again is at or near the distal end 60 and allows loop end 66 to basically be retracted into distal end 60, at least substantially. Slot 68 allows the loop to be brought to its contracted state, again without deformation exceeding its limit of elasticity, but to a small outside diameter only slightly larger than the diameter of tip 50. This is accomplished even with specialized side opening 64. Again this allows for a very small diameter tip 50, and the rounded edges of the loop end 66 for wire 52 minimizes any trauma in the insertion and removal of the tool.

It is noted that the angled side opening 64 is advantageous in that the loop end 66 extends outwardly and angularly from the longitudinal axis 70 of the instrument. Therefore, loop end 66 can be brought around the piece to be retrieved in perhaps an easier manipulation movement, than if the loop extended directly out of the tip end along axis 70 (like embodiment 10 of FIGS. 1-11). Of course, it can be appreciated that different distal ends can be utilized for different procedures according to desire.

Figures 17, 18:
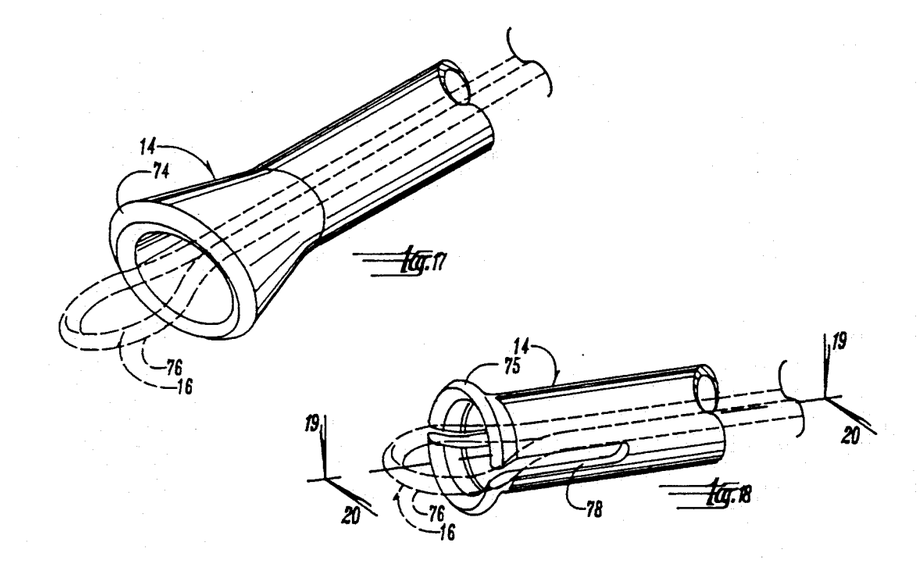
FIG. 17 is an enlarged partial perspective view of a still further alternative embodiment for the end for the surgical snare.
FIG. 18 is an enlarged perspective view of an other alternative embodiment for the tip end for the surgical snare.

Further embodiments for distal ends of the surgical snare according to the present invention are shown at FIGS. 17-18. In FIG. 17, the "receiving means" for the tip end is a somewhat flared end 74 comprising the distal end of the snare. All other components of the snare work like the embodiments of either snare 10 or snare 46 previously described.

In this case of FIG. 17, however, the flared end 74, actually comprising somewhat of a flattened flared end, allows loop end 76 to expand outwardly and contract inwardly to its smallest size without elastic deformation. However, again, it can receive the loop end 76 and substantially enclose it. The loop end again would form a rounded surface to minimize insertion or retraction trauma. The distal flared end 74 also would hold the loop end 76 somewhat rigidly therein.

The embodiment of FIG. 17 could be a retrieving snare or a cutting snare. Loop end 76 would pull tissue against the inner edge of the slot flared end 74 to cut, or to retrieve.

Figure 19:
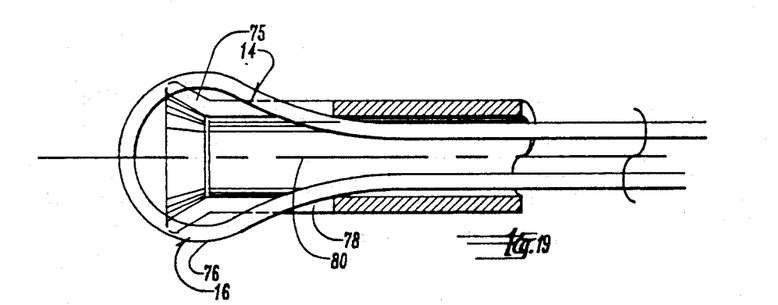
FIG. 19 is a cross sectional view taken along lines 19—19 of FIG. 18.
Figure 20:
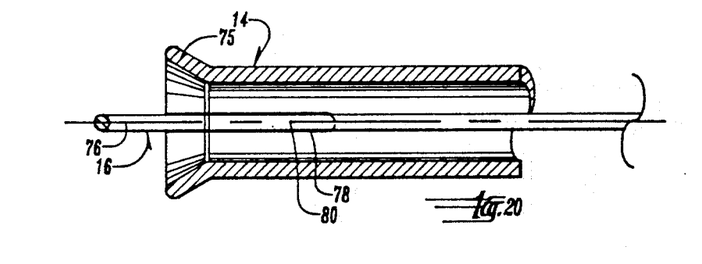
FIG. 20 is a cross sectional view taken along lines 20—20 of FIG. 18.

FIGS. 18-20 show flared more circular "trumpet" end 75 with loop end 76, but also show a slot 78 extending along longitudinal axis 80 proximally from end 75 into tip 14. Slot 78 functions essentially the same as slot 68 of snare 46 and slot 40 of snare 10 allowing the loop end 76 to be contracted and enveloped without exceeding its elastic limits. Slot 78 along with end 75 thus can comprise the "receiving means" for retrieving purposes where the loop end 76 is substantially enclosed within end 75 and yet extends slightly outside its outside diameter. This presents a rounded surface for insertion and removal, and is a simple, durable configuration.

It can therefore be seen that the invention achieves at least all of its stated objectives. The included preferred embodiments are given by way of example only, and not by way It can therefore be seen that the invention achieves at least all of its stated objectives. The included preferred embodiments are given by way of example only, and not by way of limitation to the invention, which is solely described by the claims herein. Variations obvious to one skilled in the art will be included within the invention defined by the claims.

For example, the tip of the snare does not necessarily have to be linear and can take on different configurations. Different control means and handles can be used. Moreover, different types of snare wires can be used as previously discussed. The invention is also not limited to the particular medical procedures mentioned from time to time throughout this description.

In the preferred embodiments, it is to be understood that the diameter of the tips are in the range of 6/100", with the side walls of the tip tube being around 8/1000" wide. The handles are approximately ¼" in diameter by 5" long; whereas the tips can be approximately 2" long.

In the preferred embodiment of FIGS. 12-16, the side opening 64 was angled at 35° from longitudinal axis 70 at its distal side, and 90° from the longitudinal axis 70 at its proximal side.

The slots were generally 1/10" long and slightly bigger than the outside diameter of snare wire.

What is claimed is:

1. An improved surgical snare apparatus comprising:
a snare wire having a U-shaped loop end, first and second free ends, and elongated intermediate portions;
a tip means having a hollow longitudinal bore through which extend the intermediate portions of the wire, the U-shaped loop end being reducible to a smallest outside diameter without substantial permanent deformation of the snare wire, the smallest outside diameter exceeding the diameter of the hollow longitudinal bore through the tip means;
a handle from which extends the tip means, the handle being adapted to allow manual gripping and maneuvering of the apparatus and a control means for controlling the U-shaped loop end of the snare wire between and including the smallest outside diameter and a larger outside diameter;
distal end means of the tip means for allowing constriction of the loop end to the smallest outside diameter so that the loop end is substantially retracted and nested in the distal end means in the tip means, but has outer surfaces which extend outside the distal end means, and so that the tip means is substantially closed and edges in the tip means distal end which would otherwise claw at the tissue through which the loop end and tip means must enter and exit are substantially shielded and kept away from the tissue.

2. The apparatus of claim 1 wherein the distal end means comprises a slot into which at least a portion of the loop end can be received.

3. The apparatus of claim 1 wherein the distal end means comprises a shaped end where the end is flared into an oblate hemisphere.

4. The apparatus of claim 1 wherein the distal end means comprises a generally cylindrical tubular end with a slot transversely positioned in the end.

5. The apparatus of claim 1 wherein the distal end means comprises a flared trumpet end of oblate shape including a slot transversely across the end.

6. The apparatus of claim 1 wherein the distal end means has a closed rounded surface with an entry slot located along the side of the tip means in back of the rounded end.

7. The apparatus of claim 6 wherein the entry slot is angled proximally from the side of the tip end means toward its center longitudinal axis.

8. An improved surgical snare instrument, including a wire having a loop for cutting or retrieving, opposite ends of the wire extending axially through a hollow tip into a handle member, and being attached to a movable control member, extension and contraction of the loop being controlled by the control member, the improvement comprising:
a tip end means for allowing the loop to be larger in outside diameter than the inside diameter of the hollow tip, the tip end means having a distal end including receiving means which receives a substantial part of the loop when brought to a contracted state with respect to the snare instrument, the receiving means comprising a transverse slot.

9. The instrument of claim 8 wherein the tip end means comprises a cylindrical tube end and the transverse slot of the receiving means extends proximally from the distal end.

10. The instrument of claim 8 wherein the tip end means comprises a cylindrical tube end with a rounded substantially closed outer end and the transverse slot being positioned along the side of the tip end means proximally from the closed rounded end.

11. The instrument of claim 10 wherein the transverse slot is angled inwardly and proximally from the outer surface of the tip end means.

12. An improved surgical snare instrument, including a wire having a loop for cutting or retrieving, opposite ends of the wire extending axially through a hollow tip into a handle member, and being attached to a movable control member, extension and contraction of the loop being controlled by the control member, the improvement comprising:

a tip end means for allowing the loop to be larger in outside diameter than the inside diameter of the hollow tip, the tip end means having a distal end including receiving means which receives a substantial part of the loop when brought to a contracted state with respect to the snare instrument, the receiving means comprising a flared trumpet end.

13. The instrument of claim 12 wherein the tip end means comprises a cylindrical tube end with the flared trumpet end positioned at the distal end.

14. The instrument of claim 13 further comprising a transverse slot in the flared trumpet end.

15. An improved surgical snare comprising:
handle means;
tip means;
wire means;
the tip means including a hollow interior having a diameter;
the wire means being threaded through the tip means extending out an open end of the tip means and returning through the tip means to form a loop snare at the open end;
the loop snare of the wire means being retractable to a contracted position having a contracted diameter at the open end and extendable to an expanded position;
the tip means being connected to the handle means and having loop snare receiving means to allow the loop snare to move between contracted and expanded positions without permanent deformation, the loop snare receiving means comprising a slot extending transversely across the tip means to receive the loop snare substantially into the tip means, but allowing the contracted diameter of the loop to be larger than the diameter of the hollow interior so that portions of the loop snare remain outside the hollow interior.

16. The snare of claim 15 wherein the wire means comprises a shape memory effect metallic alloy.

17. The snare of claim 16 wherein the shape effect memory material is nitinol.

18. An improved surgical snare comprising:
handle means;
tip means;
wire means;
the tip means including a hollow interior having a diameter;
the wire means being threaded through the tip means extending out an open end of the tip means and returning through the tip means to form a loop snare at the open end;
the loop snare of the wire means being retractable to a contracted position having a contracted diameter at the open end and extendable to an expanded position;
the tip means being connected to the handle means and having loop snare receiving means to allow the loop snare to move between contracted and expanded positions without permanent deformation, the loop snare receiving means comprising a flared trumpet bell shaped portion to receive the loop snare substantially into the tip means, but allowing the contracted diameter of the loop to be larger than the diameter of the hollow interior so that portions of the loop snare remain outside the hollowed interior.

19. The snare of claim 18 wherein the wire means comprises a shape memory effect metallic alloy.

* * * * *